(12) United States Patent
Langhorn

(10) Patent No.: US 8,268,383 B2
(45) Date of Patent: Sep. 18, 2012

(54) MEDICAL IMPLANT AND PRODUCTION THEREOF

(75) Inventor: Jason Langhorn, Warsaw, IN (US)

(73) Assignee: Depuy Products, Inc., Warsaw, IN (US)

(*) Notice: Subject to any disclaimer, the term of this patent is extended or adjusted under 35 U.S.C. 154(b) by 186 days.

(21) Appl. No.: 12/546,020

(22) Filed: Aug. 24, 2009

(65) Prior Publication Data

US 2010/0076569 A1  Mar. 25, 2010

Related U.S. Application Data

(60) Provisional application No. 61/098,882, filed on Sep. 22, 2008.

(51) Int. Cl.
| | |
|---|---|
| A61L 27/30 | (2006.01) |
| A61F 2/34 | (2006.01) |
| A61F 2/30 | (2006.01) |
| B01D 57/02 | (2006.01) |
| C25D 9/04 | (2006.01) |

(52) U.S. Cl. ...... 427/2.26; 427/2.1; 427/2.24; 427/2.27; 623/22.15; 623/22.17; 623/22.21; 623/22.22; 623/22.23; 204/450; 204/479; 205/316; 205/333

(58) Field of Classification Search ........... 427/2.1, 427/2.24, 2.26, 2.27; 623/22.15, 22.17, 22.21, 623/22.22, 22.23; 204/450; 205/316, 333
See application file for complete search history.

(56) References Cited

U.S. PATENT DOCUMENTS

| | | | |
|---|---|---|---|
| 3,852,045 A | 12/1974 | Wheeler et al. | |
| 4,145,764 A * | 3/1979 | Suzuki et al. | 623/23.6 |
| 4,156,943 A | 6/1979 | Collier | |
| 4,206,516 A | 6/1980 | Pilliar | |
| 4,612,160 A | 9/1986 | Donlevy et al. | |
| 4,778,474 A | 10/1988 | Homsy | |
| 4,944,760 A | 7/1990 | Kenna | |
| 4,990,163 A * | 2/1991 | Ducheyne et al. | 427/2.24 |
| 5,104,410 A | 4/1992 | Chowdhary | |
| 5,201,766 A | 4/1993 | Georgette | |
| 5,258,044 A | 11/1993 | Lee | |
| 5,368,881 A | 11/1994 | Kelman et al. | |

(Continued)

FOREIGN PATENT DOCUMENTS

EP  1923079 A1  5/2008

(Continued)

OTHER PUBLICATIONS

Maca et al. Electrophoretic deposition of alumina and zirconia. Ceramics International 30 (2004) pp. 843-852.*

(Continued)

*Primary Examiner* — Timothy Meeks
*Assistant Examiner* — Cachet Sellman
(74) *Attorney, Agent, or Firm* — Nutter McClennen & Fish LLP

(57) ABSTRACT

Medical implants exhibiting optimized mechanical properties, and methods of making such implants, are disclosed. That is, the implants are fabricated of a porous metal substrate and include coating integrated over various areas so as to provide some added or desirable property or functionality to the implant. In one embodiment, the implant is an acetabular implant with a coating applied to an internal, concave wear surface which is sized and configured to receive a head of a femur. Typically, the coating is a ceramic incorporated onto the desired area of the implant via electrophoretic deposition.

10 Claims, 5 Drawing Sheets

U.S. PATENT DOCUMENTS

| | | | |
|---|---|---|---|
| 5,549,699 | A | 8/1996 | MacMahon et al. |
| 5,549,701 | A | 8/1996 | Mikhail |
| 5,645,594 | A | 7/1997 | Devanathan et al. |
| 5,658,333 | A | 8/1997 | Kelman et al. |
| 5,766,257 | A | 6/1998 | Goodman et al. |
| 5,879,398 | A | 3/1999 | Swarts et al. |
| 6,042,780 | A | 3/2000 | Huang |
| 6,059,949 | A | 5/2000 | Gal-Or et al. |
| 6,087,553 | A | 7/2000 | Cohen et al. |
| 6,090,144 | A | 7/2000 | Letot et al. |
| 6,293,971 | B1 | 9/2001 | Nelson et al. |
| 6,319,285 | B1 | 11/2001 | Chamier et al. |
| 6,852,272 | B2 | 2/2005 | Artz et al. |
| 7,094,259 | B2 | 8/2006 | Tarabichi |
| 2003/0050705 | A1* | 3/2003 | Cueille et al. ............... 623/22.24 |
| 2003/0171818 | A1* | 9/2003 | Lewallen ................... 623/22.22 |
| 2003/0171820 | A1 | 9/2003 | Wilshaw et al. |
| 2005/0069629 | A1 | 3/2005 | Becker et al. |
| 2005/0123672 | A1 | 6/2005 | Justin et al. |
| 2006/0178749 | A1 | 8/2006 | Pendleton et al. |
| 2006/0198943 | A1* | 9/2006 | Kumar ......................... 427/2.27 |
| 2006/0231402 | A1 | 10/2006 | Clasen et al. |
| 2006/0271191 | A1 | 11/2006 | Hermansson |
| 2007/0078521 | A1 | 4/2007 | Overholser et al. |
| 2008/0188942 | A1 | 8/2008 | Brown et al. |
| 2008/0199720 | A1 | 8/2008 | Liu |
| 2009/0054985 | A1* | 2/2009 | Anderson .................. 623/17.11 |
| 2009/0084491 | A1 | 4/2009 | Uthgenannt et al. |
| 2009/0088859 | A1 | 4/2009 | Hazebrouck et al. |
| 2009/0125114 | A1 | 5/2009 | May et al. |
| 2010/0042225 | A1 | 2/2010 | Shur |
| 2010/0100190 | A1 | 4/2010 | May et al. |
| 2010/0100191 | A1 | 4/2010 | May et al. |
| 2010/0262144 | A1 | 10/2010 | Kelman et al. |

FOREIGN PATENT DOCUMENTS

| | | |
|---|---|---|
| EP | 1923079 A1 * | 5/2008 |
| GB | 1065354 A | 4/1967 |
| WO | 03039609 A1 | 5/2003 |

OTHER PUBLICATIONS

European Search Report for EP09170648 dated Mar. 1, 2010.
Partial European Search Report for EP09170648 date Jan. 31, 2010.
Maca, et al., "Electrophorectic deposition of alumina and zirconia I. Single-component systems", Ceramics International, vol. 20, pp. 843-852, 2004.

\* cited by examiner

MEDICAL IMPLANT AND PRODUCTION THEREOF

RELATED APPLICATION(S)

This application claims priority pursuant to 35 U.S.C. §119 (e) to U.S. Provisional Patent Application Ser. No. 61/098,882, filed on Sep. 22, 2008, entitled "Medical Implant And Production Thereof," the entirety of which being incorporated herein by reference thereto.

FIELD

The present disclosure relates to medical implants and production thereof.

BACKGROUND

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint. For example, in a total hip arthroplasty an acetabular cup may be implanted in the pelvis to replace the natural acetabulum. In many instances, it is also necessary to replace the head of the femur with a prosthetic femoral head.

Surgical success and long term patient comfort depend to a large extent on the proper alignment of the prosthetic joint components as well as the interaction between the wear surfaces of the acetabular cup and the femoral head. High strength materials with good wear properties and low coefficient of friction offer the most promise for long term joint replacement solutions.

Currently, the wear surfaces of joint prostheses are made from a variety of materials. Among the most prevalent are metals and metal alloys, polymers, and ceramics. Ceramic on metal and ceramic on ceramic wear surfaces are currently common. One challenge facing designers of joint prostheses such as hip prostheses is that the properties that contribute to the proper integration of an acetabular cup, for example, into bone include relatively high porosity of the surface that will be embedded in bone. However, the wear surface should be a smooth, strong surface with a low coefficent of friction.

There is thus a need for joint prostheses and methods of making joint prostheses that are able to exhibit different properties for different portions of the prosthesis.

SUMMARY

Various aspects of a medical implant are provided herein. In one such aspect, the medical implant includes a porous substrate having a cup-shaped portion defining a wear surface which is sized and configured to receive a complementary articulating component. The concave wear surface of the implant includes a substantially smooth coating of a desired thickness disposed over at least a portion thereof. Furthermore, the coating of the implant can penetrate a plurality of pores of the wear surface of the implant to facilitate anchoring of the coating to the substrate. In one embodiment the implant is in the form of an acetabular cup and the complementary articulating component is a femoral head. As such, the wear surface can be a concave, recessed surface.

The coating can include various materials that exhibit the desired properties of hardness, smoothness, and a low coefficient of friction. For example, the coating can be a ceramic coating (e.g., alumina, zirconia, and mixtures thereof). Alternatively, the coating can be a biocompatible electrophoretic deposited glass and/or porcelain ceramic. Additionally, the coating can also include virtually any material capable of being applied as desired, and also capable of providing and/or exhibiting some desired physical and/or mechanical property.

The porous substrate can be formed of a wide range of materials. For example, the porous substrate can be a metal foam structure. The porous substrate could also be a layered composite of porous and dense regions (e.g., a porous substrate on the inner portion for bonding the electrophoretic coating, a solid titanium or cobalt chrome substrate, and a porous outer surface for fixation to bone). In such an embodiment, the metal foam structure can include various metals such as titanium, cobalt, molybdenum, tungsten, stainless steel, and alloys thereof. One exemplary material is an alloy of titanium, such as Ti-6A1-4V. Furthermore, to aid in the coating process, at least a portion of the porous substrate can be formed of a material capable of maintaining an electric charge (e.g., thereby allowing for electrophoretic deposition).

Various aspects of a method for fabricating a medical implant are also provided. In one such aspect, the method includes providing a porous metal substrate (e.g., an acetabular cup) which includes a wear surface capable of maintaining an electric charge. A colloidal suspension can be placed in communication with the wear surface, and an electric charge across the wear surface can be established. The charge should be of a magnitude sufficient to establish a desired flow of charged particles from the colloidal suspension to the wear surface, and the electric charge is maintained until a desired coating is formed on the wear surface.

The charged particles can be any type of particle capable of responding to the electric charge established across the wear surface of the implant. For example, the particles can be ceramic particles (e.g., alumina or zirconia), biocompatible electrophoretically deposited glasses, and/or porcelain ceramics.

In one exemplary embodiment, the coating can be integrated into the substrate in such a manner so as to substantially anchor the coating to the substrate. For example, the coating process (e.g., electrophoretic deposition) can be optimized such that the coating penetrates into a plurality of pores of the porous substrate thereby anchoring the coating to the substrate.

In yet another aspect, a method of fabricating an acetabular cup implant is provided which includes providing a porous metal substrate having a cup element which defines an internal wear surface with the cup element being sized and configured to receive a head of a femur. The method also includes electrophoretically depositing a coating over a desired surface area of the wear surface. Various reaction parameters (e.g., temperature, pressure, magnitude of electric charge, etc.) can be selected and optimized to provide a coating of a desired thickness and/or shape so as to provide the desired mechanical propert(ies) to the finished implant.

DETAILED DESCRIPTION

Certain exemplary embodiments will now be described to provide an overall understanding of the principles of the structure, function, manufacture, and use of the implant and methods of production disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Medical implants with optimal mechanical properties are provided herein. That is, the implants provided herein are formed of a porous substrate configured to provide a desired strength and/or other mechanical property to the implant. Additionally, a coating can be incorporated over various areas of the substrate. During fabrication, the coating can be selected and applied to the substrate for the purpose of modifying and/or optimizing the mechanical properties of those select areas. For example, the coating can be applied to a wear surface portion of the substrate which is configured to receive another implant and/or boney structure thereby allowing the structures to move freely (or at least with greater ease) relative to one another and/or optimizing the friction coefficient between the structures. As as an additional benefit, due to the porous nature of the underlying substrate, the coating can be applied to the substrate in such a manner as to penetrate the pores and thus effectively anchor the coating to the substrate thereby providing a low mass, substantially monoblock implant which is free (or at least at a reduced risk) of any of the complications or failures of a modular implant (e.g., fretting wear, corrosion products, etc.). Further, the coating, when applied to the porous substrate, results in a smooth, continuous surface.

Figure 1:
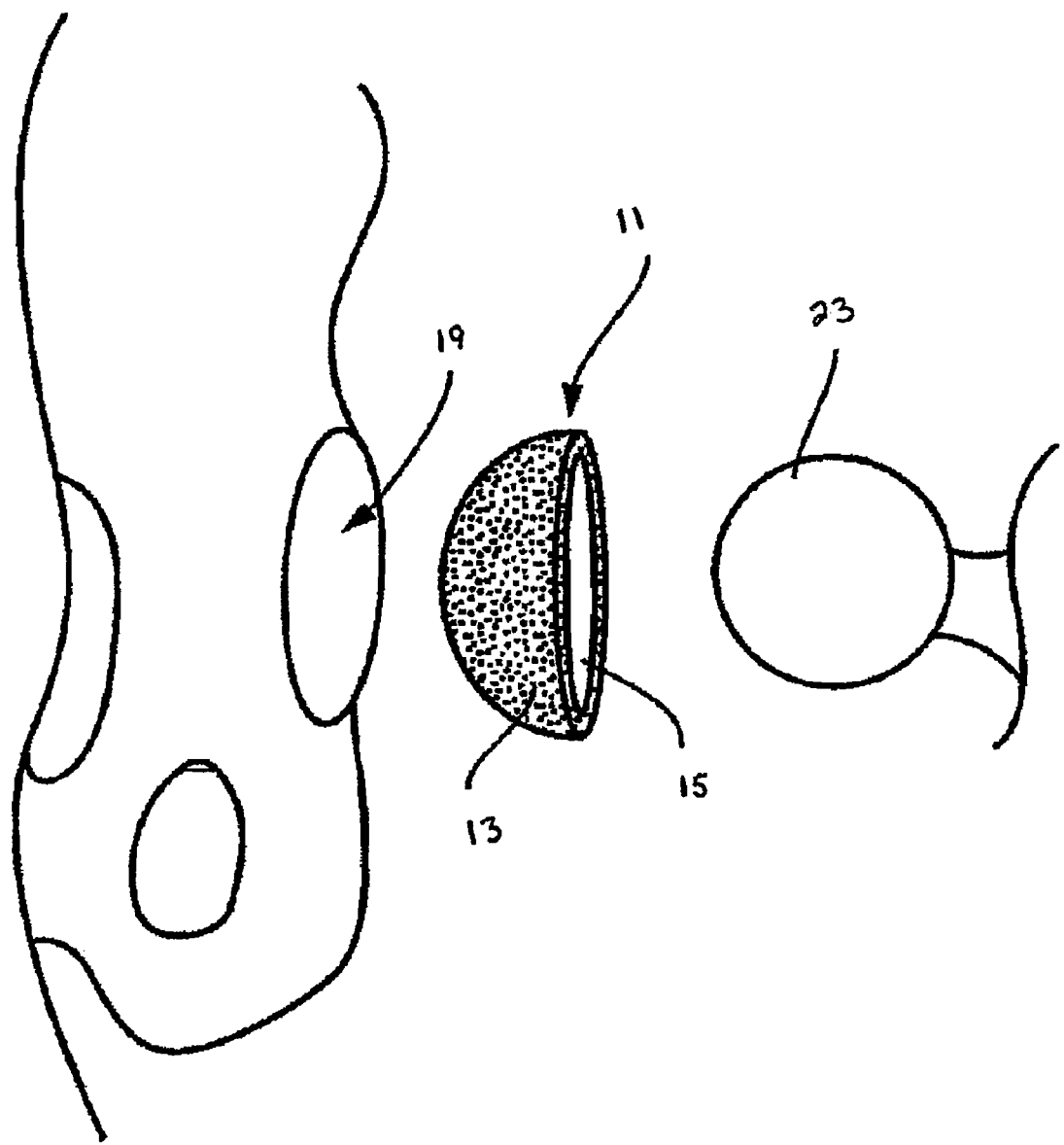
FIG. 1 is a representation of an exemplary embodiment of an acetabular implant.

Various types and forms of implants are within the spirit and scope of the present disclosure. For example, this disclosure can include any implant which requires a hard wear bearing surface on one side and a porous ingrowth surface on the other side (e.g., knee components such as tibial trays, spine disc implants, shoulder cups, ankle components, finger joints, etc.). In an exemplary embodiment, the implant can be a joint prosthesis such as an acetabular cup. FIG. 1 illustrates an exemplary embodiment in which the substrate is a prosthetic acetabular cup 11 defining an internal, concave surface 15 which is sized and configured to receive a femoral head 23. Additionally, an external portion 13 of the acetabular cup 11 can be sized and configured to be implanted in a portion 19 of the patient's pelvis. Although only an acetabular cup is illustrated, and the implant is described with reference to an acetabular cup, one skilled in the art will appreciate that this disclosure is applicable to numerous types of medical implants and joint prostheses.

The implants provided herein include a coating deposited over select areas of a porous substrate. The identity, positioning, and/or thickness of the coating is selected so as to optimize the mechanical properties of the implant. In the example of the acetabular cup 11 of FIG. 1, the coating can be applied over the entire or at least a portion of the interior, concave wear surface 15 thereby optimizing the ability of the implant 11 to receive and move relative to the femoral head 23 of the patient's femur 21 by decreasing the coefficient of friction. While the coating decreases the coefficient of friction of the wear surface 15, the external surface remains porous and substantially rough, thereby providing an external surface that enhances bone ingrowth.

Various types of coatings are within the spirit and scope of the present disclosure. For example, the coating can be a ceramic coating, a biocompatible glass coating, a porcelain ceramic coating, enamels, etc. In an exemplary embodiment, the coating is a ceramic such as alumina, zirconia, or some combination thereof. Also, the coating can be selected based on the method of applying the coating to the substrate. For example, in one embodiment, the coating is applied via electrophoretic deposition. Thus, in such an embodiment, the coating can be formed from a colloidal suspension having particles (e.g., ceramics) that are able to be driven in a desired direction in response to an electric charge applied across the suspension.

As noted above, one exemplary technique for applying the coating is via electrophoretic deposition (EPD). EPD is a term for a broad range of industrial processes which include electrocoating, cathodic electrodeposition, and electrophoretic coating, or electrophoretic painting. A characteristic feature of EPD is that colloidal particles suspended in a liquid medium migrate under the influence of an electric field (electrophonesis) and are deposited onto an electrode. All colloidal particles that can be used to form stable suspensions and that can carry a charge can be used in electrophoretic deposition, including materials such as polymers, dyes, ceramics and metals. The process is useful for applying materials to any electrically conductive surface (e.g., the porous metal substrate). The materials which are being deposited (e.g., the ceramic coating) are the major determining factor in the actual processing conditions and equipment which may be used.

EPD has a number of advantages over other coating techniques. For example, the process applies coatings which generally have a very uniform coating thickness. Additionally, complex fabricated objects can easily be coated, both inside cavities as well as on the outside surfaces of an object. Thus, EPD can deposit the coating within the pores of the internal concave surface thereby effectively anchoring the coating to the substrate. Further, the process can be automated and thereby require less human labor than other coating processes.

In use, EPD typically includes various pre-coating, coating, and coating steps. For example, the object to be coated (e.g., the porous metal substrate) is first prepared for coating, such as by cleaning the surface. To initiate the coating process itself, the part to be coated can be submerged within a container or vessel which holds the coating bath or solution. Once the area to be coated is placed into communication with the solution/suspension, an electrical current can be applied through an electrode placed within the EPD bath, such as in contact with the part to be coated. Typically, voltages in the range of about 25 to about 400 volts DC are used in electocoating or electrophoretic painting applications. The object to be coated (e.g., the implant) serves as one of the electrodes, and a set of "counter-electrodes" within the bath are used to complete the circuit. After deposition, the object is normally rinsed to remove the undeposited materials. The rinsing process may utilize an ultrafilter to dewater a portion of the bath from the coating vessel to be used as rinse material. If an ultrafilter is used, all of the rinsed off materials can be returned to the coating vessel allowing for high utilization efficiency of the coating materials, as well as reducing the amount of waste discharged into the environment. Finally, a drying or annealing and sintering process is normally used following the rinse. That is, the drying process can be performed for up to about 24 hours at a temperature of from about room tempterature to about 100° C. The drying process is followed by an annealing process which is performed at about 800° C. for about 1 hour to about 2 hours. The coating can then be sintered at a temperature in the range of about 1200 ° C. to about 1500 ° C. for an amount of time capable of producing the desired results and/or properties. The typical titanium foam ("Ti foam") substrate firing is typically about 1370° C. Therefore, if the substrate is a Ti foam substrate these processes may need to be optimized (e.g., adjustment of firing temperatue, addition of sintering aids, e.g., glass formers, firing at increased pressures, microwave assisted sintering, etc.).

Production of a medical implant, such as an acetabular cup, via EPD provides numerous advantages. For example, EPD can effectively coat interior recessed regions to effectively penetrate and anchor to a porous substrate. Another property of EPD is that the coating will deposit to fill in any imperfections on the substrate surface. The coating (e.g., the ceramic) will be deposited until the electric charge over the surface of the substrate is reduced to a level under which no more deposition will occur. Therefore, deposition over a porous irregular metal surface can result in a smooth, continuous coated surface which can be polished. Thus, a monoblock porous substrate acetabular cup implant with EPD deposited coating on the wear interface will have a microstructure which inherently has a high coefficient of friction at the mounting interface to the hip bone, will inherently be porous for beneficial bone in-growth at the bone interface, and also have a ceramic wear interface with a low coefficicent of friction for bearing against a metal or ceramic femoral head.

Substrate materials can be formed by the deposition/fixation of porous type coatings to the surface of a a solid metal component for subsequent deposition of the EPD ceramic. Such porous structure coatings can be formed by sintering small balls or beads to the surface of the component (e.g., Porocoat®) and/or the attachment (usually by sintering) of irregularly shaped materials such as powder (e.g., Gription®), wire, etc. Those skilled in the art will appreciate that various such substrates are within the spirit and scope of the present disclosure.

Various porous substrates can be utilized to form the implant. For example, the substrate can be fabricated from processes that involve combining a liquid-extractable pore-forming agent (PFA) with a metal powder in the presence of a liquid in which the PFA is soluble. It is understood that possible PFA/liquids combinations include PFAs that are soluble in organic liquids paired with an organic liquid, or PFAs that are soluble in non-organic liquids paired with a non-organic liquid.

In certain embodiments, the liquid is aqueous. For example, the liquid can include at least about 75 weight percent water, more preferably at least about 90 weight percent water, even more preferably at least about 95 weight percent water. Representative liquids include water (such as reverse osmosis water, deionized water, distilled water, and/or deoxygenated water) or an aqueous carbohydrate solution.

In other embodiments, as disclosed in pending U.S. patent application Ser. No. 11/677,140, filed on Feb. 21, 2007, the entirety of which being incorporated herein by reference, the liquid can be an aqueous solution of polyhydric alcohols (e.g., a glycerol solution), a solution of hydrophilic polymers, or any other solution capable of acting as an effecting homogenizing aid.

Although the amount of liquid used will depend upon the nature of the metal powder and PFA and the processing conditions employed, it has been found that the use of about 450 µL to about 1050 µL per 100 $cm^3$ of the pre-compaction mixture, and more preferably about 600 µL to about 750 µL per 100 $cm^3$ of pre-compaction mixture, is particularly useful.

PFAs according to the present invention are particulate materials that are soluble in a fluid of interest. Representative PFAs include sodium chloride, ammonium chloride, calcium chloride, magnesium chloride, aluminum chloride, potassium chloride, nickel chloride, zinc chloride, ammonium bicarbonate, sodium hydrogen phosphate, sodium dihydrogen phosphate, potassium dihydrogen phosphate, potassium hydrogen phosphate, potassium hydrogen phosphite, potassium phosphate, magnesium sulfate, potassium sulfate, alkaline earth metal halides, crystalline carbohydrates (including sucrose and lactose classified as monosaccharides, disaccharides, and trisaccharides), polyvinyl alcohol (PVA), polyethylene oxide, a polypropylene wax (such those available from Micro Powders, Inc., Tarrytown, N.Y., under the PROPYL-TEX trademark), sodium carboxymethyl cellulose (SCMC), polyethyleglycol-polypropylene-polyethyleneglycol copolymers (PEG-PPG-PEG, such as those available from BASF, Ludwigshafen, Germany under the PLURONIC trademark), and combinations thereof.

The PFA can be present in a wide variety of particle sizes and particle size distributions suitable to produce a pore size and pore size distribution. Exemplary particle size ranges are from about 200 µm to about 600 µm, from about 200 µm to about 350 µm, and from about 350 µm to about 550 µm.

Virtually any type of metal powder known in the field of powder metallurgy can be used in the methods of the present disclosure. Exemplary metal powders are those that are formed from titanium, cobalt, chromium, nickel, magnesium, tantalum, niobium, zirconium, aluminum, copper, molybdenum, tungsten, stainless steel, or alloys thereof (e.g., Co-Cr alloy). In one embodiment, the metal powder is titanium or a titanium alloy such as Ti-6A1-4V.

The metal powder also can be present in a wide variety of particle sizes and particle size distributions. Exemplary particle size ranges are from about 20 µm to about 100 µm, from about 25 µm to about 50 µm, and from about 50 µm to about 80 µm.

Those skilled in the art will recognize that the proportions of metal powder and PFA will vary depending upon the type of structure sought to be produced. In certain embodiments, the ratio of metal powder to PFA is in the range of about 40:60 to about 10:90, and more preferably about 25:75.

After the metal powder, PFA, and liquid are mixed, the resulting mixture is compacted to form a green body. The compacting step can be carried out via any of the many techniques known in the art, including uniaxial die and punch, biaxial die and punch, or cold or rubber isostatic press. In certain embodiments of the invention, the compacting pressure is from about 20 ksi to about 60 ksi, preferably from about 30 ksi to about 45 ksi. Once formed, the green body may be machined by any of the techniques known in the art, such as cutting, milling, turning, drilling, and/or facing.

The PFA can be removed from the green body using any liquid capable of dissolving the PFA, thus revealing the metal skeleton. As with the liquid that is mixed with the metal powder and PFA prior to compaction, the dissolving liquid can be aqueous, such as water (e.g., reverse osmosis water, deionized water, distilled water, and/or deoxygenated water) or an aqueous carbohydrate solution. The liquid that is used to dissolve the PFA can be the same as or different than the liquid that is mixed with the metal powder and PFA prior to compaction, e.g., the chemical identity of the components in the respective liquids and/or their relative proportions can be the same or different.

The dissolution step can be effected by, for example, immersing the green body in a bath containing a liquid in which it is soluble or contacting the green body with a stream of that liquid. The temperature range for the liquid used in the dissolution step can be above its freezing point but below its boiling point, and preferably is in the range of about 50° F. to about 176° F. (about 10° C. to about 80° C.). Certain steps known to affect dissolution may be implemented, for example, the bath solution can be circulated or portions of the bath solution periodically replaced with fresh solution.

The metal skeleton obtained upon removal of the PFA may also be machined, such as by cutting, milling, turning, drilling, and/or facing the skeleton.

The metal skeleton typically will be sintered to impart the desired properties. While all suitable sintering conditions are contemplated, sintering for titanium or Ti-6A1-4V alloy typically will be performed at temperatures of from about 2100° F. to about 2700° F. (preferably about 2500° F.) and/or for about 2 hours to about 10 hours (preferably about 3 hours to about 6 hours).

Figure 2:
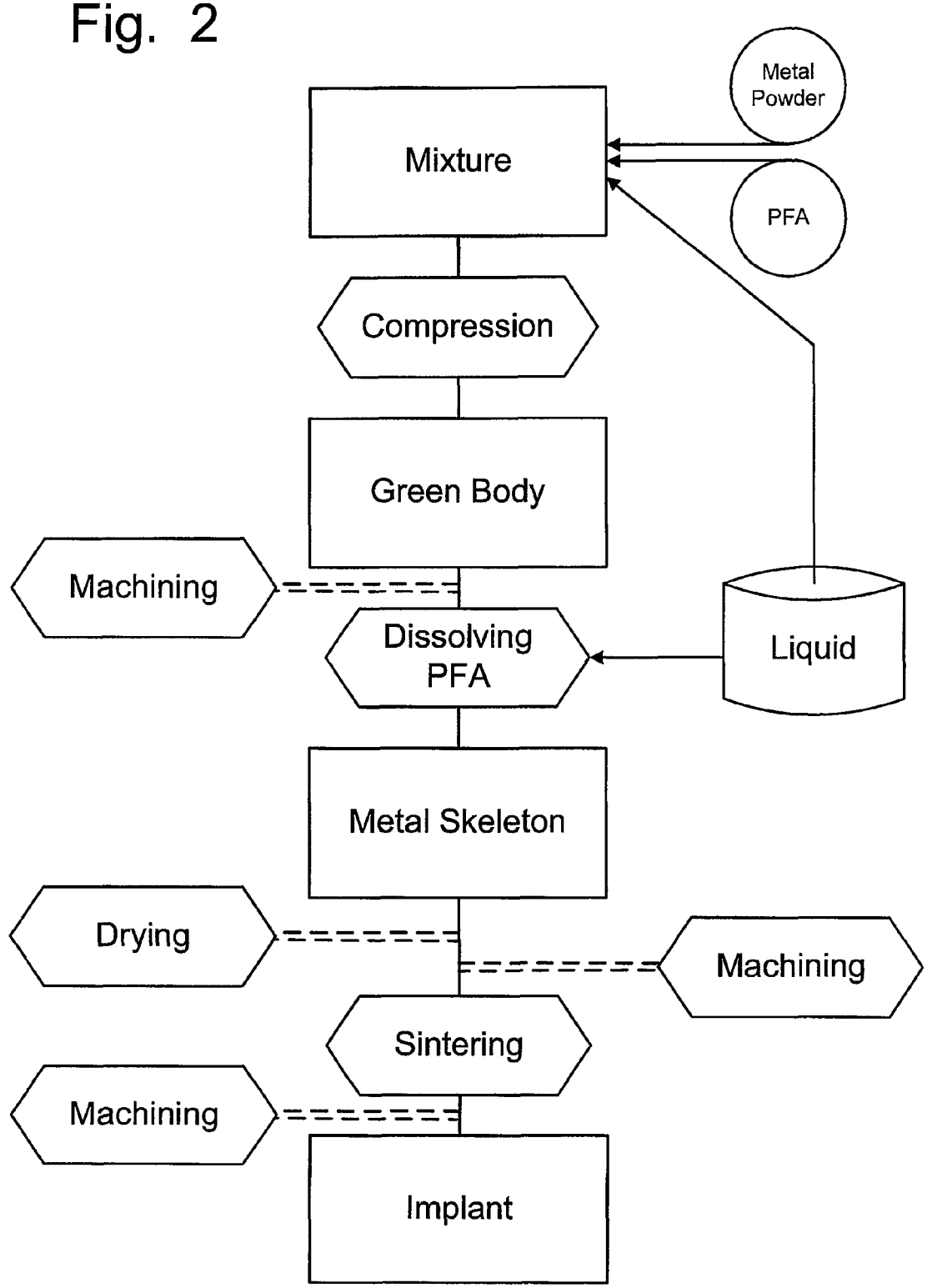
FIG. 2 is a schematic of a process of making a porous substrate according to one embodiment of the present disclosure.
Figure 3:
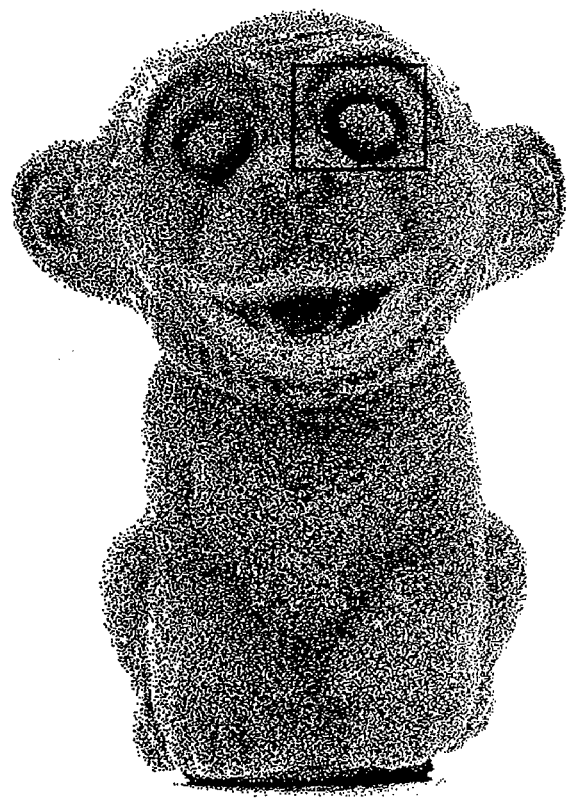
FIG. 3 is an image of a sintered metal foam structure.
Figure 4:
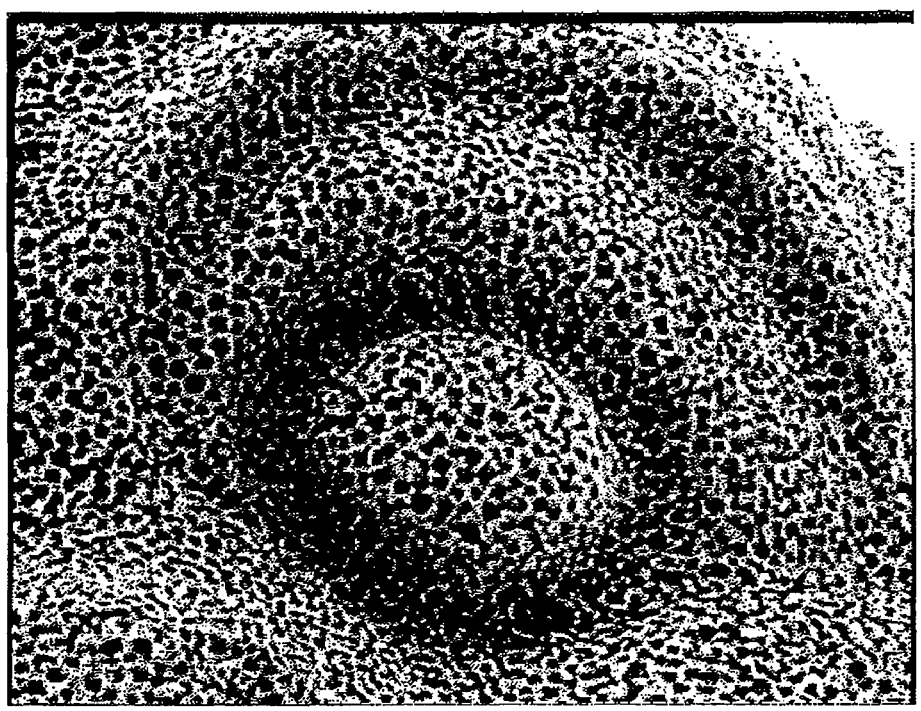
FIG. 4 is an image of the sintered metal foam structure of FIG. 3 in a side view.
Figure 5:
FIG. 5 is an image of the sintered metal foam structure of FIG. 3 in a detail view.
Figure 6:
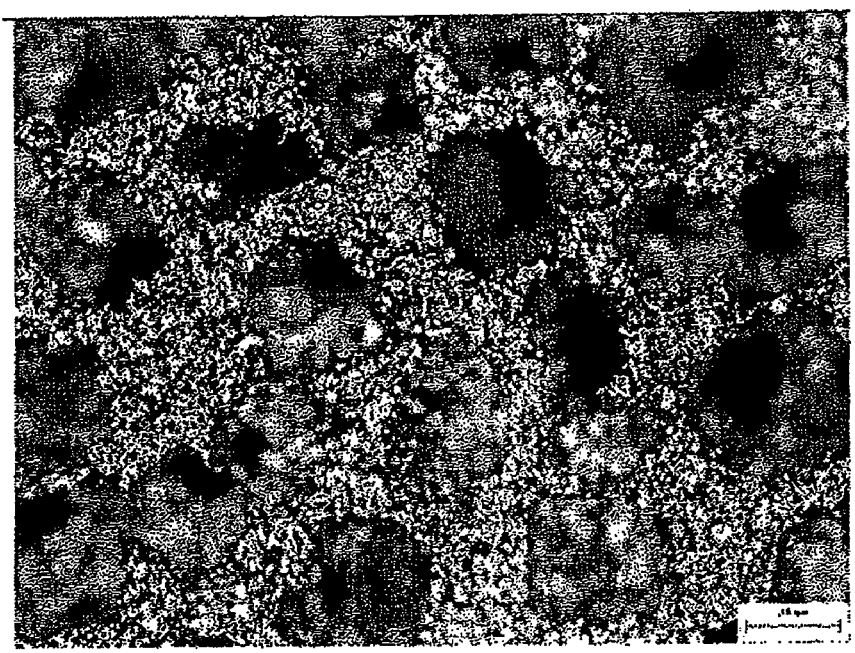
FIG. 6 is an optical microscope image of the sintered metal foam structure of FIG. 3.

The methods disclosed herein can be used, for example, to produce metal implants that include a porous surface. Referring now to FIG. 2, certain processes for making such implants are depicted. Metal powder, PFA, and a liquid in which the PFA is soluble are combined to form a mixture. The mixture is compressed (for example via uniaxial, multi-axial, or isostatic compaction) in a shaped mold to form a green body. The mold determines the shape of the implant, and thus should generally be of a desired shape to avoid or at least minimize the need for substantial machining. The PFA is dissolved from the green body through contact with a liquid in which the PFA is soluble to form a metal skeleton. Optionally, the metal skeleton may be machined and/or dried to remove residual liquid. The metal skeleton is sintered, and afterwards optionally machined to form a porous metal implant. Those skilled in the art are aware of suitable shapes for such implants and the properties that they should possess, for example suitable compressive yield strength. Although the first liquid and second liquid are depicted as coming from the same source in FIG. 2, it is understood that the liquids need not be identical, only that they each be a liquid in which the pore-forming agent is soluble.

The surface of the porous metal implant may be roughened. Methods of roughening include at least one of grit blasting, etching, or plasma sputtering and are known in the art. One exemplary method of etching is the etching method of U.S. Patent Application Publication No. 2004/0167633, the entirety of which being incorporated herein by reference. A suitable method of grit blasting uses a water soluble grit, such as NaCl, to blast against the implant, thus allowing for removal of impacted grit from the pores by dissolution in an aqueous liquid.

In certain embodiments, the present disclosure provides metal implants or other types of metal skeletons having a porosity of from about 60% to about 85% (preferably about 65% to about 75%) as measured by volume, the forced intrusion of liquid mercury, and cross-section image analysis. Porous ingrowth surfaces like Porocoat® may be as low as about 30% to about 35% volume porosity but is typically in the range of about 45% to about 50% volume porosity. Gription is typically about 60% to about 65% volume porosity. It is understood that the porosity can be a product of metal to PFA ratio, PFA size, or a combination thereof. Lower porosity surfaces may be easier to deposit a continuous, dense ceramic surface onto by electrophoretic deposition so a "graded structure" (i.e., highly porous on the bone side and less so on the deposition side) or a Porocoat® or roughened surface may be helpful.

In one embodiment, exemplary pure titanium skeletons are those that have a tensile strength of at least about 35 MPa (as measured by the standard tension testing-ASTM E8-99), or a flexural yield strength of at least about 90 MPa (as measured by three-point bend testing—ASTM E290-97a), and/or a compressive yield strength of at least about 65 MPa (as measured by monotonic compression testing—ASTM E9-89a) at a porosity of about 65%. Particularly useful pure titanium skeletons are those that have a tensile strength of at least about 40 MPa (measured via ASTM E8-99), or with a flexural yield strength of at least about 110 MPa (measured via ASTM E290-97a), and/ or with a compressive yield strength of at least about 75 MPa (measured via ASTM E9-89a) at a porosity of about 65%.

It is understood that titanium alloys can be used to obtain greater strengths. Exemplary titanium alloy skeletons are those that have a tensile strength of at least about 60 MPa (measured via ASTM E8-99), or with a flexural yield strength of at least about 120 MPa (measured via ASTM E290-97a), and/or with a compressive yield strength of at least about 90 MPa (measured via ASTM E9-89a) at a porosity of about 65%. Particularly useful titanium alloy skeletons are those that have a tensile strength of at least about 90 MPa (measured via ASTM E8-99), or with a flexural yield strength of at least about 180 MPa (measured via ASTM E290-97a), and/or with a compressive yield strength of at least about 110 MPa (measured via ASTM E9-89a) at a porosity of about 65%.

While not intending to be bound by theory, it is believed that porosity, metal powder particle size, and sintering temperature are important factors contributing to the strength of the resulting structure.

Methods of fabricating medical implants with desired mechanical properties are also provided herein. For example, a method is provided for fabricating components of a hip joint prosthesis, such as an acetabular cup. Initially, the method can include fabricating or obtaining a substrate (e.g., a porous substrate) shaped in the form of an acetabular cup which exhibits some degree of mechanical strength and/or toughness. Next, various portions or areas of the substrate can be further processed to impart some additional desired mechanical properties. For example, the porous substrate can include a wear surface on an interior portion of the acetabular cup which is sized and configured to receive a femoral head. In an exemplary embodiment, a coating can be applied to this internal wear surface to optimize the hardness and smoothness of the wear surface, and thus to provide a wear surface with an inherently low coefficient of friction.

In an exemplary embodiment, the coating (e.g., a ceramic) is applied to the surface of the cup by electrophoretic deposition. The various benefits and/or advantages of electrophoretic deposition are described above. As known to those skilled in the art, the various system parameters (e.g., temperature, pressure, etc.) can be optimized in view of the surface area of the implant to be coated and/or the desired thickness to be deposited. Typically, the composition includes aluminum oxide ($Al_2O_3$), zirconium oxide ($ZrO_2$), or a mixture of both. The composition of the ceramic/liquid suspension is typically prepared as follows: $Al_2O_3$ and/or $ZrO_2$ ceramic powder having particle sizes of about 0.5 to about 1 micron (e.g. alumina powders: CT3000SG powder supplied by Alcoa or Product code 4001103 supplied by Almatis) is combined with a liquid for suspension. Such liquids include isopropanol (very low water content needed in dispersing media). Additionally, monochloroacetic acid having greater than or equal to about 12 weight % appears to change the charge on suspended powder from positive ve to negative ve and leads to very flat highly dense deposits on anodes. Typically, EPD is performed using a substantially constant current (e.g., at a current of about 5 mA). To control location of the coating, a teflon cup fixture can be utilized to hold and mask the areas of the implant (e.g., the acetabular cup) which are not to be coated. Following coating, the implant can be washed to remove any residual solution, and the implant can be annealed and sintered at a desired temperature and/or pressure.

In alternative embodiments, the coating (e.g., ceramic) can be delivered to the substrate via injection molding or plasma spraying. Injection molding is a manufacturing technique for making parts from both thermoplastic and thermosetting plastic materials in production. Molten plastic is injected at high pressure into a mold, which is the inverse of the product's shape. After a product is designed, molds are made from metal, usually either steel or aluminium, and precision-machined to form the features of the desired part.

Plasma spraying, a method of thermal spraying, is a materials processing technique for producing coatings and free-standing parts using a plasma jet. Deposits having thickness from micrometers to several millimeters can be produced from a variety of materials, including metals, ceramics, polymers and composites. The material to be deposited (feedstock)—typically as a powder, sometimes as a liquid, suspension or wire—is introduced into the plasma jet, emanating from a plasma torch. In the jet, where the temperature is on the order of 10,000K, the material is melted and propelled towards a substrate. There, the molten droplets flatten, rapidly solidify, and form a deposit. Commonly, the deposits remain adherent to the substrate as coatings; free-standing parts can also be produced by removing the substrate. There are a large number of technological parameters that influence the interaction of the particles with the plasma jet and the substrate and therefore the deposit properties. These parameters include feedstock type, plasma gas composition and flow rate, energy input, torch offset distance, substrate cooling, etc.

EXAMPLES

The following provides various examples of methods for producing a porous substrate. These examples are not intended to be limiting in any manner.

Example 1

Commercial pure titanium powder (Phelly Materials, Inc. Bergenfield, N.J., USA) particle size: about 45 µm to about 75 µm and NaCl (Fisher Scientific International Inc. Hampton, N.H., USA) particle size: about 250 µm to about 425 µm, as a PFA, were mixed in a ratio of approximately 25:75 Ti:PFA by volume. Reverse osmosis water was added in an amount corresponding to about 700 µL per 100 $cm^3$ of Ti:PFA mixture. The mixture was added to a mold and compressed into a green body at a compaction pressure of about 22 ksi. The green body was placed in a water bath until the NaCl dissolved. The resulting metal skeleton was dried at 65° C. for about 4 hours, and then sintered at 1204° C. for 2 hrs. The sintered metal foam structure is depicted in FIGS. 3-6, which show a highly porous metal foam structure in a complex shape.

Example 2

Figure 7:
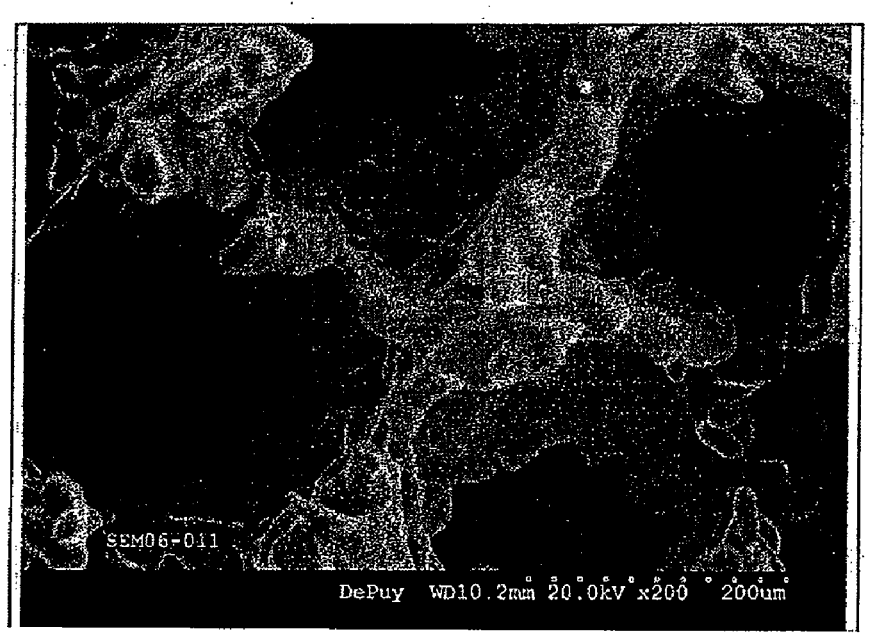
FIG. 7 is a scanning electron microscope (SEM) image of a sintered metal foam structure at 200× magnification.
Figure 8:
FIG. 8 is a SEM image of the sintered metal foam structure at 700× magnification.

Commercial pure titanium powder particle size: about 45 µm to about 75 µm and NaCl particle size: about 250 µm to about 425 µm, as a PFA, were mixed in a ratio of approximately 20:80 Ti:PFA by volume. Reverse osmosis water was added in an amount corresponding to about 700 µL per 100 $cm^3$ of Ti:PFA mixture. The mixture was added to a mold and compressed into a green body at a compaction pressure of 23.6 ksi. The green body was placed in a water bath until the NaCl dissolved. The resulting metal skeleton was first dried in the oven as in Example 1 and then sintered at 1371° C. for 3 hrs. The sintered metal foam structure is depicted in FIGS. 7-8.

Example 3

Titanium powder (about 32 µm to about 45 µm (500-350 mesh)) and NaCl (about 425 µm to about 500 µm) were mixed in a ratio of approximately 25:75 Ti:PFA by volume. Reverse osmosis water was added in an amount corresponding to about 700 µL per 100 $cm^3$ of Ti:PFA mixture. The mixture was added to a mold and compressed into a green body at a compaction pressure of 30 ksi. The green body was placed in a water bath for about 12 hours to allow the PFA to dissolve. The resulting metal skeleton was sintered at 1731 ° C. for 6 hrs. The sintered metal foam structures had about 65% porosity. The compressive yield strength and flexural yield strength were 82 MPa and 180 MPa, respectively, determined by performing the standard compression test and three-point bend test following ASTM E9-89a and ASTM E290-97a.

Example 4

Titanium powder (about 32 µm to about 45 µm (500-350 mesh)) and NaCl (250 µm to about 300 µm) were mixed in a ratio of approximately 25:75 Ti:PFA by volume. Reverse osmosis water was added in an amount corresponding to about 700 µL per 100 $cm^3$ of Ti:PFA mixture. The mixture was added to a mold and compressed into a green body at a compaction pressure of 45 ksi. The green body was placed in a water bath for about 12 hours to allow the PFA to dissolve. The resulting metal skeleton was sintered at 1371° C. for 6 hrs. The sintered metal foam structures had about 65% porosity. The compressive yield strength and flexural yield strength were 77 MPa and 196 MPa, respectively, determined as described above with reference to Example 3.

In the foregoing specification, the concepts have been described with reference to specific embodiments. Many aspects and embodiments have been described above and are merely exemplary and not limiting. After reading this specification, skilled artisans appreciate that other aspects and embodiments are possible without departing from the scope of the disclosure. Moreover, one skilled in the art will appreciate that various modifications and changes can be made without departing from the scope of the disclosure as set forth in the claims below. Accordingly, the specification and figures are to be regarded in an illustrative rather than a restrictive sense, and all such modifications are intended to be included within the scope of the present disclosure.

One skilled in the art will appreciate further features and advantages of the presently disclosed devices and methods based on the above-described embodiments. Accordingly, the disclosed embodiments are not to be limited by what has been particularly shown and described, except as indicated by the appended claims. All publications and references cited herein are expressly incorporated herein by reference in their entirety.

We claim:

1. A method of fabricating a medical implant, comprising:
providing a porous metal substrate which includes a wear surface capable of maintaining an electric charge;
positioning a colloidal suspension in communication with the wear surface;
establishing an electric charge across the wear surface of a magnitude which drives a flow of charged, ceramic particles from the colloidal suspension to the wear surface at a desired rate, wherein the ceramic particles include alumina or zirconia; and
maintaining the electric charge until a desired coating is formed on the wear surface.

2. The method of claim 1, wherein the coating penetrates a plurality of pores of the porous substrate thereby anchoring the coating to the substrate.

3. The method of claim 1, wherein the wear surface is recessed and concave.

4. The method of claim 1, wherein the substrate is in the form of an acetabular cup.

5. The method of claim 1, wherein the porous metal substrate comprises a material selected from the group consisting of titanium, cobalt, molybdenum, tungsten, stainless steel, and alloys thereof.

6. The method of claim 1, wherein the porous metal substrate is Ti-6A1-4V.

7. A method of fabricating an acetabular cup implant, comprising:
providing a porous metal substrate having cup element which defines a concave wear surface, the cup element being sized and configured to receive a head of a femur; and
electrophoretically depositing a ceramic coating over a desired surface area of the wear surface.

8. The method of claim 7, wherein the ceramic is selected from the group of ceramics consisting of alumina, zirconia, and mixtures thereof.

9. The method of claim 7, wherein the porous metal substrate comprises a material selected from the group consisting of titanium, cobalt, molybdenum, tungsten, stainless steel, and alloys thereof.

10. The method of claim 7, wherein the porous metal substrate is Ti-6A1-4V.

* * * * *